(12) United States Patent  
Beutter

(10) Patent No.: US 7,867,265 B2
(45) Date of Patent: Jan. 11, 2011

(54) BONE CLAMP

(75) Inventor: Florian Beutter, Solothurn (CH)

(73) Assignee: Synthes USA, LLC, West Chester, PA (US)

( * ) Notice: Subject to any disclaimer, the term of this patent is extended or adjusted under 35 U.S.C. 154(b) by 992 days.

(21) Appl. No.: 11/299,117

(22) Filed: Dec. 8, 2005

(65) Prior Publication Data

US 2006/0142771 A1  Jun. 29, 2006

Related U.S. Application Data

(63) Continuation of application No. PCT/CH03/000369, filed on Jun. 11, 2003.

(51) Int. Cl.
*A61B 17/064* (2006.01)
(52) U.S. Cl. ......................... 606/324; 606/75
(58) Field of Classification Search .................. 606/60, 606/72, 75, 151, 157, 219, 324, 329
See application file for complete search history.

(56) References Cited

U.S. PATENT DOCUMENTS

| | | | |
|---|---|---|---|
| 3,960,147 A | | 6/1976 | Murray |
| 4,434,796 A | * | 3/1984 | Karapetian et al. ............ 606/75 |
| 4,454,875 A | * | 6/1984 | Pratt et al. ..................... 606/75 |
| 4,719,917 A | * | 1/1988 | Barrows et al. ............. 606/220 |
| 4,723,540 A | * | 2/1988 | Gilmer, Jr. ..................... 606/75 |
| 4,887,601 A | * | 12/1989 | Richards ..................... 606/219 |
| 4,994,063 A | * | 2/1991 | Garner ......................... 606/75 |
| 5,026,390 A | * | 6/1991 | Brown ........................ 606/221 |
| 5,053,038 A | * | 10/1991 | Sheehan ....................... 606/75 |
| 5,246,443 A | * | 9/1993 | Mai ............................. 606/78 |
| 5,454,814 A | * | 10/1995 | Comte ......................... 606/75 |

(Continued)

FOREIGN PATENT DOCUMENTS

DE    202 04 513 U1    9/2002

(Continued)

OTHER PUBLICATIONS

International Search Report for International Application No. PCT/CH03/00369, mailed Jan. 20, 2004, German language version.

(Continued)

*Primary Examiner*—Thomas C Barrett
*Assistant Examiner*—Larry E. Waggle, Jr.
(74) *Attorney, Agent, or Firm*—Fay Kaplun & Marcin, LLP

(57) ABSTRACT

A bone clamp moving bone segments relative to each other. The clamp comprises a first and second branch and a bridge connecting the first and second branch. The bone clamp may have a first, undeformed state, where the branches may be angled or substantially parallel with respect to each other. The bone clamp may have a second, deformed state, where the branches may be moved from the first state. The bone clamp may be deformed using an instrument such as pliers. When the bone clamp is in the deformed state, the branches may be inserted into bone segments. Thereafter, the instrument may be disengage from the bone clamp and the clamp may return to its undeformed state. While returning to the first, undeformed, state the bone clamp may apply compressive or distraction forces on the bone segments, thereby moving the bone segments relative to each other.

31 Claims, 1 Drawing Sheet

U.S. PATENT DOCUMENTS

| | | | |
|---|---|---|---|
| 5,660,188 A * | 8/1997 | Groiso | 128/898 |
| 5,779,707 A * | 7/1998 | Bertholet et al. | 606/75 |
| 5,785,713 A * | 7/1998 | Jobe | 606/75 |
| 5,853,414 A * | 12/1998 | Groiso | 606/75 |
| 5,993,476 A * | 11/1999 | Groiso | 606/219 |
| 6,059,787 A * | 5/2000 | Allen | 606/75 |
| 6,325,805 B1 * | 12/2001 | Ogilvie et al. | 606/75 |
| 6,342,055 B1 * | 1/2002 | Eisermann et al. | 623/17.16 |
| 6,767,356 B2 * | 7/2004 | Kanner et al. | 606/213 |
| 2001/0002436 A1 * | 5/2001 | Bowman et al. | 606/72 |

FOREIGN PATENT DOCUMENTS

| | | |
|---|---|---|
| EP | 0 752 238 A1 | 1/1997 |
| EP | 0 852 128 A1 | 7/1998 |
| FR | 2 694 696 A1 | 2/1995 |

OTHER PUBLICATIONS

International Search Report for International Application No. PCT/CH03/00369, mailed Jan. 20, 2004, English language translation of the German language version.

International Preliminary Examination Report for International Application No. PCT/CH03/00369, completed Nov. 11, 2005, German language version.

International Preliminary Examination Report for International Application No. PCT/CH03/00369, completed Nov. 11, 2005, English language translation of the German language version.

* cited by examiner

BONE CLAMP

CROSS-REFERENCE TO RELATED APPLICATION

This application is a continuation of pending International Patent Application PCT/CH2003/000369, filed Jun. 11, 2003, which is incorporated by reference herein in its entirety.

FIELD OF THE INVENTION

The present invention relates to an apparatus and method for treating bone fractures and, more particularly, to a deformable bone clamp for moving bone segments relative to each other.

BACKGROUND OF THE INVENTION

Bone clamps are used to engage bone segments on opposite side of a fracture and hold them together. Current bone clamps made of memory metal alloy are known and generally have a transformation temperature in the body temperature range. These clamps have disadvantages. For example, current clamps must be cooled/frozen in a refrigerator or, after being implanted, heated with a special heating apparatus, such as a coagulator, which may lead to necroses. Due to the extremely high or low temperatures during or after the implantation, the tissues surrounding the bone may be injured, so that the blood supply may be affected and, as a result, the fracture may heal slowly, if at all. Moreover, in the event that the clamp is implanted improperly, the clamp cannot be reused. Therefore, it is desirable to provide a bone clamp, which does not require cooling and heating to implant in bone and which can be reused.

SUMMARY OF THE INVENTION

A bone clamp is described having a first branch which may have a first end and second end, a second branch which may have a first end and a second end, and a bridge which may connect the first branch and the second branch. The bridge and branches may be made of a single piece of material or may be separate components which may be joined together. The bone clamp may have a first state and a second state. The first ends of the branches may be a first distance apart and the second ends of the branches may be a second distance apart. The first and second distances may be different in at least one of the first and second state. In one embodiment, in the first state, the first distance may be less than the second distance. In another embodiment, in the first state, the first distance may be greater than the second distance. In such embodiment, in the second state, the first distance may be substantially equal to the second distance. In yet another embodiment, in the first state, the first distance may be substantially equal to the second distance and, in the second state, the first distance may be greater than or less than the second distance. The first ends of the bone clamp may be a first distance (D1) apart in the first state and may be a second distance (D2) apart in the second state. The distance (D1) in the first state may be more or less than the distance (D2) in the second state depending upon whether a compressing or distracting force is desired.

The bridge may be elastically deformable and may be a closed curve shape such as, for example, elliptical. In other embodiments, the bridge may be rhomboidal or diamond shaped. Alternatively, the bridge may be substantially U-shaped or S-shaped. Furthermore, the bridge may be mechanically deformed so that at least a portion of the first and second branches may move relative to each other. The bridge may be located in a first plane, and the first and second branch may be located in a second plane. The first and second plane may be at an angle relative to each other and may intersect.

The branches may be shaped and configured to enable insertion into bone. For example, the first ends of the first and second branches may be pointed or blunted. In other embodiments, the first ends of the first and second branches may be tapered towards the first ends. Moreover, the first and second branch may have a cross-section which is circular or polygonal (e.g., rectangular, pentagon, hexagon, etc.) in shape. In order to prevent removal of the bone clamp from bone, the branches may also have a three-dimensional, structured surface such as transverse ribs or transverse grooves.

The bone clamp may have a first state (i.e., undeformed state) and a second state (i.e., deformed state). In the first state, the bone clamp or, more specifically, pieces or portions thereof such as, for example, the bridge, may be in an unstressed condition, and in the second state, the bone clamp or, more specifically, pieces or portions thereof such as, for example, the bridge, may be in a stressed condition. In the first state, in one embodiment, the branches may be angled with respect to each other. For example, the first ends may converge towards each other such that the first distance may be less than the second distance. Alternatively, in the first state, the first ends may diverge away from each other such that the first distance may be greater than the second distance. In another embodiment, in the first state, the branches may be parallel to each other. In the second state, the first ends and/or the second ends may be moved away from each other, thereby increasing the distance between the first ends and/or second ends. Alternatively, in the second state, the first end and/or second ends may be moved towards one another, thereby decreasing the distance between the first ends and/or the second ends. In some embodiments, in the second state, the branches may be aligned with respect to each other (e.g., the branches may be parallel with respect to each other).

The bone clamp may be made of, for example, a memory metal alloy. In one embodiment, the memory metal alloy may be a nickel-titanium alloy in which the nickel content may be between about 45 percent and about 55 percent and the titanium content may be between about 45 percent and about 55 percent. In other embodiments, the bone clamp may be made of a nickel-free elastic material. For example, the bone clamp may be made of plastic such as polyether ether ketone or carbon fiber-reinforced polyether ether ketone. The material used may have a non-linear stress-strain curve.

The bone clamp may be used to move bone segments relative to each other. The method of inserting a bone clamp may comprise providing a bone clamp comprising a first branch having a first end and a second end, a second branch having a first end and a second end, and a bridge operably connecting the first and second branches. Prior to inserting the bone clamp into bone, holes may be create in bone for receiving the first and second branches. Thereafter, the bridge may be deformed so that the bone clamp moves from the first, unstressed state to the second, stressed state. As the bridge is deformed, the first and second branches may move relative to each other. The bridge may be deformed using an instrument (e.g., pliers). The bridge may be deformed so that the distance at the ends where the bridge connects to the branches is expanded or contracted. The instrument may be used to increase or decrease the distance between the first and second branches and align the first and second branches with respect to each other.

The step of moving the first and second branch relative to each other may comprise increasing or decreasing the distance between the first ends of the first and second branches. Moreover, the step of moving the first and second branch relative to each other may comprise increasing or decreasing the distance between the second ends of the first and second branches. Moving the first and second branches relative to each other may change the state of the bone clamp from the first state to the second state or vice versa. Once the bridge has been deformed and the branches are moved with respect to each other, the first branch may be inserted into a first bone segment and the second branch may be inserted into a second bone segment. With the bone clamp positioned in bone, the instrument, which is used to deform the bone clamp, may be disengaged from the clamp and the clamp may return to or move towards the first, unstressed state. As the clamp returns to the first state, the clamp may exert a compression or distraction force on the first and second bone segments, thereby causing the bone segments to move towards or away from each other.

BRIEF DESCRIPTION OF THE DRAWINGS

The bone clamp, and its method of operation and use may be better understood by reference to the following drawings, wherein like references numerals represent like elements. The drawings are merely exemplary to illustrate the structure, operation and method of use of the bone clamp and certain features that may be used singularly or in combination with other features and the invention should not be limited to the embodiments shown.

DETAILED DESCRIPTION OF THE INVENTION

Figure 1:
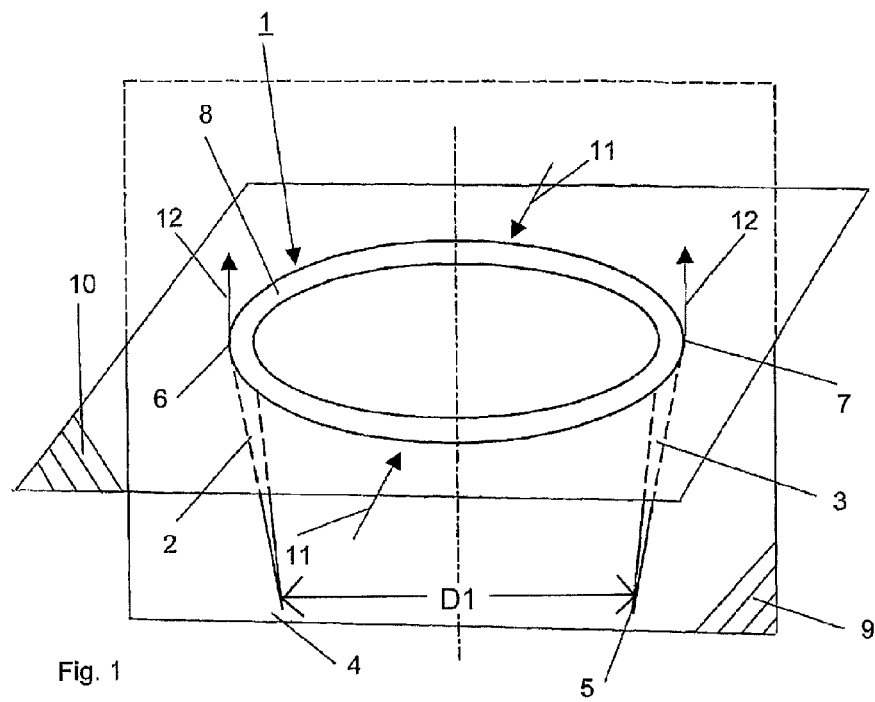
FIG. 1 is a perspective view of the bone clamp of the present invention in a first state.

As shown in FIG. 1, the bone clamp 1 may include two branches 2, 3. The branches 2, 3 may have a first, free end 4, 5 and a second, rear end 6, 7, respectively, and may define a plane 9. The rear ends 6, 7 may be connected to one another by a bridge 8, which may be elastically deformable. The branches 2, 3 and bridge 8 may be made of a single piece of material or may be separate components which may be joined together. It should, however, be understood that those of ordinary skill in the art will recognize many modifications and substitutions which may be made to various elements of the present invention.

Figure 2:
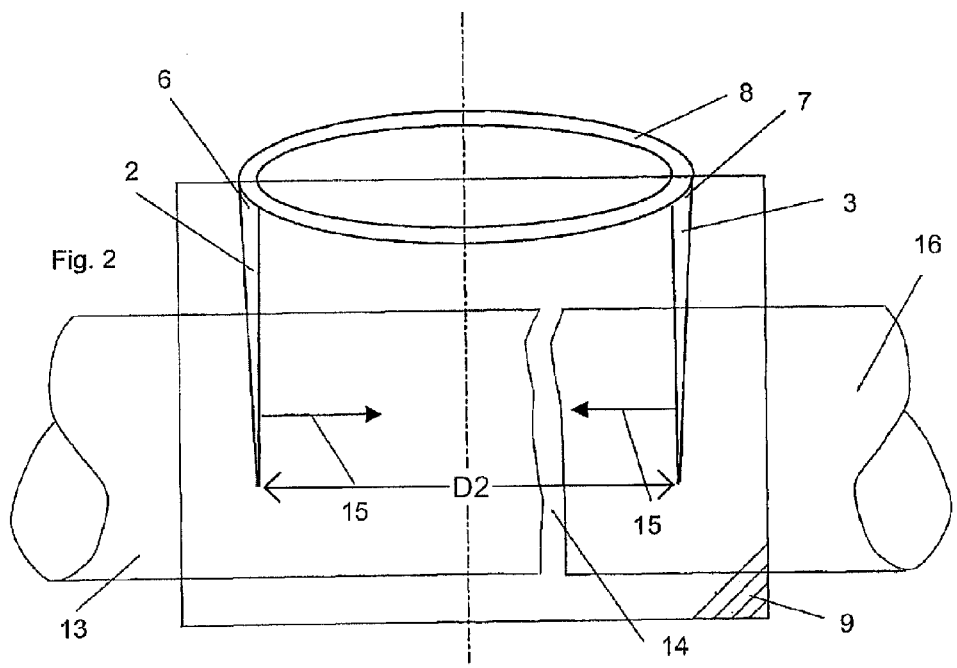
FIG. 2 is a perspective view of the clamps of FIG. 1 in a second state being inserted in bone segments.

The bone clamp 1 may have a first, tension-free state (i.e., undeformed, unstressed state) such as shown in FIG. 1 and a second, tensioned state (i.e., deformed, stressed state) such as shown in FIG. 2. In the undeformed state, the free ends 4, 5 may be a first distance apart and the rear ends 6, 7 may be a second distance apart. In the first, undeformed state, the branches 2, 3 may converge so that the first distance is less than the second distance (i.e., the free ends 4, 5 may be closer to one another than the rear ends 6, 7). In another embodiment, in the first, undeformed state, the branches 2, 3 may diverge so that the first distance is greater than the second distance (i.e., the free ends 4, 5 may be farther away from each other than the rear ends 6, 7). In the second, deformed state, the first and second distance may be substantially the same (e.g., the branches 2, 3 may be substantially parallel to each other). In yet another embodiment, in the undeformed state, the first and second distance may be substantially the same and, in the deformed state, the first and second distance may be different (e.g., the first distance may be greater than the second distance or the second distance may be greater than the first distance).

The free ends 4, 5 may be configured so that the branches 2, 3 are capable of being inserted into bone. For example, the free ends 4, 5 may be pointed. Alternatively, the cross-section of the two branches 2, 3 of the bone clamp 1 may taper towards its free ends 2, 3 (e.g., from the rear ends 4, 5 or a distance from the rear ends 4, 5 to the free ends 2, 3). In another embodiment, the free ends 4, 5 may be blunt. In such an embodiment, a surgeon may be required to pre-drill holes in bone to insert the branches 2, 3. A bone clamp 1 with blunt ends 4, 5 may be used biocortically so that there is no injury to soft parts. Furthermore, the branches 2, 3 of the bone clamp 1 may have a three-dimensionally structured surface, for example, in the form of transverse ribs or transverse grooves. Such a construction may prevent the bone clamp 1 from disengaging or slipping out of bone after implantation.

The branches 2, 3 may have a length between about 5 mm and about 20 mm. Moreover, in one embodiment, the branches 2, 3 may have a circular cross-section. In other embodiments, the cross-section of the branches 2, 3 may be non-circular (e.g., rectangular or polygon). The cross-section of the branches 2, 3 may have a dimension which may be less than or equal to about 2.0 mm and, more preferably, less than or equal to about 1.6 mm such that the area of the cross-section of the branches 2, 3 may be less than or equal to about 2.5 $mm^2$ and, more preferably, less than or equal to about 2.0 $mm^2$. Such dimension may result in branches 2, 3 which are less invasive.

The free ends 4, 5 of the branches 2, 3 which may be inserted into the bone may be a first distance D1 apart in the unstressed state and a second distance D2 apart in the stressed state. First distance D1 may be more or less than second distance D2 depending upon whether a compression force or a distraction force is desired to be applied across two respective bone segments or fragments that the free ends 4, 5 are inserted within.

Moreover, the bridge 8 which connects the branches 2, 3 may have a length of between about 8 mm and about 30 mm. The bridge 8 may connect to the branches 2, 3 at the rear ends 6, 7 or along the length of the branches 2, 3. The bridge 8 may be positioned in a plane 10, which may be at an angle (e.g., perpendicular or tangential) with respect to the plane 9 of the branches 2, 3. The bridge 8 may be substantially rhomboidal, diamond-shaped, U-shaped or S-shaped or may be configured to have a closed curve shape. For example, in one embodiment, the bridge 8 may be elliptical in shape and may have a major axis and a minor axis. The branches 2, 3 may be connected at end points of the major axis.

As shown in FIG. 2, using an instrument (not shown), the bridge 8 may be deformed elastically such that the distance between the rear ends 6, 7 of the two branches 2, 3, respectively, may be increased and, at the same time, the branches 2, 3 may be aligned essentially parallel to each other. Such deformation may result from compressing or squeezing the bridge 8 in the region between the branches 2, 3, as indicated by the two arrows 11 in the plane 10. The compression/squeezing of the bridge 8 in the direction of the arrows 11 may cause flattening of the elliptical shape. In addition, the bridge 8 may be deformed by bending the bridge 8 in the region of the rear ends 6, 7 of the branches 2, 3 in the direction as indicated by arrows 12 in the plane 9 so that the free ends 4, 5 may move relative to the region between the two branches 2, 3. The bending of the bridge 8 in the direction of the arrows 12 may result in a spreading of the branches 2, 3, so that the branches 2, 3 are aligned parallel to each other (i.e., the bridge 8 and/or branches 2, 3 may be moved so that the free ends 4, 5 of the branches 2, 3 may be spread apart, thereby increasing the first distance).

The bone clamp 1 may be made of various materials. It should be noted that in some embodiment, the bone clamp 1 may be made of a material having a nonlinear stress-strain diagram. In one embodiment, the bone clamp 1 may be made of a memory metal alloy such as, for example, a nickel-titanium alloy in which 45%<Ni<55%, 45%<Ti<55% and x+y=100%. Such a material may be particularly biocompatible and highly elastic. Moreover, a memory metal alloy may have a transformation temperature of at least about 50° C. and, more preferably, at least about 80° C. about. Typically, the transformation temperature may be at least about 100° C. and, most preferably, at least about 120° C. In an embodiment where a memory metal is used, those skilled in the art will appreciate that the compression action of the bone clamp 1 is not based on the memory effect. As such, the present invention provides the advantage that a refrigerator or heating apparatus may be unnecessary in order to use the bone clamp 1. In this way, damage to the tissue due to temperature changes/effects may be avoided.

In an alternative embodiment, the bone clamp 1 may be made from a nickel-free, elastic material (e.g., plastic), which may be advantageous for those patients, who are allergic to nickel. For example, the bone clamp 1 may be made of a polyether ether ketone (PEEK) or a carbon fiber-reinforced PEEK.

In use, the bone clamp 1 may be moved from an unstressed state to a stressed state and may be inserted into bone in the stressed state. Thereafter, while inserted in bone, the bone clamp 1 may apply pressure to the bone segments and, as the bone segments move, the bone clamp 1 may become less stressed (i.e., stress may be alleviated by movement of the components of the bone clamp 1). Thus, as the branches 2, 3 move, the bone clamp 1 may change to a less stressed state. A surgeon may select a bone clamp 1 of a certain size. In one embodiment, holes may be pre-drilled into bone for inserting the branches 2, 3. An instrument, such as a double drill bushing with an adjustable distance, may be used for maintaining particular distances in between holes. The branches 2, 3 and the bridge 8 of the bone clamp 1 may be simultaneously tensioned with a suitable tensioning instrument (not shown). For example, pliers, may be used to elastically deform the bone clamp 1. Specifically, the pliers may be used to simultaneously compress and deform the bridge 8 so that the branches 2, 3 of the bone clamp 1 may be moved away from each other and, at the same time, aligned essentially parallel to each other. The pliers may, however, also be constructed in such a manner, that the enlargement of the distance between the branches 2, 3 and their parallel alignment may take place independently of each other.

After tensioning, the bone clamp 1 may be introduced into the adjacent bone segments 13, 16 in the second, tensioned state shown in FIG. 2. In an embodiment with pre-drilled holes, the branches 2, 3 may be inserted in the holes. It should be noted that at the upper end of the branches 2, 3, proximate the transition to the bridge 8, the branches 2, 3 may be aligned parallel to each other without having to bend the bridge 8 upward out of plane 10 or turned away from the branches 2, 3. By inserting the branches 2, 3 into bone segments 13, 16, uniform distribution of the compression force along the branches 2, 3 may be ensured. When the tensioning instrument (e.g., pliers) is removed, the elastically deformed bone clamp 1 may be relaxed and may move towards its original, undeformed configuration (i.e., the bone clamp 1 may attempt to assume its first, tension-free state). In the process, the branches 2, 3 may exert a compressive force on the bone gap 14 between the two bone fragments 13, 16, as indicated by arrows 15 in the plane 9. Accordingly, the gap 14 between bone segments 13 and 16 may be held under constant compression, which may promote healing of the fracture. It should be noted that in the compressed state, the branches 2, 3 may exert a compressive force of less than or equal to about 1 MPa. In particular, the branches 2, 3 may exert a compressive force of at least about 2 kPa and, more preferably, at least about 5 kPa.

Moreover, in the compressed state, the width of the bridge 8 may be less than or equal to about 6 mm and, more preferably, less than or equal to about 5 mm. As a result, the bone clamp 1 may become less invasive, especially when used in the area where there are only a few soft parts and a broader clamp could lead to irritations of the soft parts (e.g., in areas of the hand, foot and face). Such dimensions may also have cosmetic advantages as larger clamps may be noticeable through the skin.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A bone clamp comprising:
    a first branch having a first end and a second end;
    a second branch having a first end and a second end; and
    a bridge lying in a first plane and operably connecting the first and second branches at the seconds ends thereof, the bridge biasing the bone clamp toward an unstressed state in which the first ends of the first and second branches are separated from one another by a first distance, the bridge being structured so that, when temporarily deformed through the application of a force directed substantially along a first line connecting the first and second branches, the first and second branches are moved to a first stressed state in which they are separated by a second distance, and, when temporarily deformed through the application of a force directed substantially along a second line perpendicular to the first line, the first and second branches are angularly moved to a second stressed state in which they are separated by a third distance, the bias of the bridge returning the bone clamp toward the unstressed state when the applied force is removed therefrom.

2. The clamp of claim 1, wherein the bridge has a shape selected from the group consisting of elliptical, rhomboidal, diamond, U-shaped, S-shaped and closed curve.

3. The clamp of claim 1, wherein the bridge is elastically deformable.

4. The clamp of claim 1, wherein the first and second branch are positioned in a second plane, wherein the second plane is at an angle with respect to the first plane and the first and second planes intersect.

5. The clamp of claim 1, wherein the first and second branch have a cross-section having a shape selected from the group consisting of circular and polygonal.

6. The clamp of claim 1, wherein the first and second branches are shaped and configured to enable insertion into a bone.

7. The clamp of claim 6, wherein the first ends of the first and second branches have a shape selected from the group consisting of pointed, tapered towards the first ends, and blunt.

8. The clamp of claim 1, wherein the bone clamp is made of a material which has a nonlinear stress-strain curve.

9. The clamp of claim 1, wherein the bone clamp is made of a material selected from the group consisting of memory metal alloy and plastic.

10. The clamp of claim 9, wherein the memory metal alloy is a nickel-titanium alloy.

11. The clamp of claim 1, wherein the bone clamp is made from a nickel-free, elastic material.

12. The clamp of claim 11, wherein the nickel-free elastic material is selected from the group of consisting of polyether ether ketone and carbon fiber-reinforced polyether ether ketone.

13. The clamp of claim 1, wherein the first and second branches have a three-dimensional, structured surface.

14. The clamp of claim 13, wherein at least one of the first and second branches comprises one of transverse ribs and transverse grooves.

15. The clamp of claim 1, wherein in the unstressed state, the first and second branches are substantially parallel to each other.

16. The clamp of claim 1, wherein in one of the first and second stressed states, the first and second branches are substantially parallel to each other.

17. A bone clamp for joining bone segments comprising:
a first branch having a first free end and a first rear end;
a second branch having a second free end and a second rear end; and
a mechanically deformable bridge operably connecting the first and second branches, the bridge biasing the bone clamp toward an unstressed state in which the first and second branches are angled with respect to each other prior to insertion into the bone segments, the bridge being structured so that, when temporarily deformed through the application of a force substantially along a first line connecting the first and second branches, the first and second branches are moved from the unstressed state while maintaining the angled disposition of the first and second branches substantially unchanged, the bridge being structured so that, when temporarily deformed through the application of a force applied substantially along a second line perpendicular to the first line, the first and second branches are angularly moved from the unstressed state, the bias of the bridge returning the bone clamp toward the unstressed state after removal of a force applied to the bridge, wherein a plane housing the first and second branches is substantially perpendicular to a plane in which the bridge resides when deformed and when in the unstressed state.

18. The clamp of claim 17, wherein in one of the first and second stressed states, the first and second branches are parallel relative to each other.

19. The clamp of claim 17, wherein the bridge has a shape selected from the group consisting of elliptical, rhomboidal, diamond, U-shaped, S-shaped and closed curve.

20. The clamp of claim 17, wherein the first and second branches are shaped and configured to enable insertion into a bone.

21. The clamp of claim 17, wherein the bone clamp is made of a material selected from the group consisting of memory metal alloy and plastic.

22. A method of implanting a bone clamp comprising:
providing a bone clamp comprising:
a first branch having a first end and a second end;
a second branch having a first end and a second end; and
a mechanically deformable bridge operably connecting the first and second branches, the bridge biasing the bone clamp toward an unstressed state wherein a first distance between first ends of the first and second branches is smaller than a second distance between second ends of the first and second branches, the bridge being structured to be temporarily deformed to a first stressed state through the application of a force substantially along a first line connecting the first and second branches, and to be temporarily deformed to a second stressed state different from the first stressed state when subjected to a force along a line perpendicular to the first line, wherein the first and second branches are angularly spread apart while in the second stressed state,
deforming the bridge to one of the first and second stressed states and inserting the first end of the first branch into a first bone segment and the first end of the second branch into a second bone segment; and
releasing the bone clamp so that the bias of the bridge urges the bone clamp toward the unstressed state moving the first and second bone segments relative to one another in a desired direction.

23. The method of claim 22 further comprising drilling holes in the bone segments for receiving the first and second branches.

24. The method of claim 23 further comprising providing an instrument for deforming the bridge.

25. The method of claim 24, wherein the instrument is pliers.

26. The method of claim 24, further comprising using the instrument to move the bone clamp from the unstressed to one of the first and second stressed states.

27. The method of claim 22, wherein the deforming the bone clamp comprises compressing the bridge.

28. The clamp of claim 1, wherein one of the second distance and the third distance is greater than the first distance.

29. The clamp of claim 1, wherein the second distance is less than the third distance.

30. The clamp of claim 1, wherein the second distance is greater than the third distance.

31. The clamp of claim 2, wherein the first and second branches are on opposed ends of a major axis of the bridge.

* * * * *